(12) United States Patent
Kolluri et al.

(10) Patent No.: US 6,746,403 B2
(45) Date of Patent: Jun. 8, 2004

(54) PHYSIOLOGICAL-SIGNAL-ANALYSIS DEVICE FOR MEASURING A BLOOD PRESSURE AND METHOD

(75) Inventors: Sai Kolluri, Tampa, FL (US); Lawrence T. Hersh, Tampa, FL (US); Richard Medero, Tampa, FL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 29 days.

(21) Appl. No.: 09/683,911

(22) Filed: Mar. 1, 2002

(65) Prior Publication Data

US 2002/0082507 A1 Jun. 27, 2002

Related U.S. Application Data

(63) Continuation-in-part of application No. 09/678,650, filed on Oct. 4, 2000, now Pat. No. 6,423,010.

(51) Int. Cl.$^7$ .................................................. A61B 5/02
(52) U.S. Cl. ....................... 600/485; 600/300; 600/301; 600/508; 600/509
(58) Field of Search ................................ 600/300–301, 600/485–507, 508, 509

(56) References Cited

U.S. PATENT DOCUMENTS

| | | | |
|---|---|---|---|
| 4,262,674 A | | 4/1981 | Uemura et al. |
| 4,349,034 A | | 9/1982 | Ramsey, III |
| 4,360,029 A | | 11/1982 | Ramsey, III |
| 4,543,962 A | | 10/1985 | Medero et al. |
| 4,638,810 A | | 1/1987 | Ramsey, III et al. |
| 4,649,930 A | * | 3/1987 | Groch et al. ............ 600/508 |
| 4,889,133 A | | 12/1989 | Nelson et al. |
| 4,949,710 A | | 8/1990 | Dorsett et al. |
| 5,014,714 A | | 5/1991 | Millay et al. |
| 5,033,472 A | * | 7/1991 | Sato et al. ............... 600/504 |
| 5,238,001 A | | 8/1993 | Gallant et al. |
| 5,392,781 A | * | 2/1995 | Phillipps et al. ......... 600/493 |
| 5,404,878 A | | 4/1995 | Frankenreiter et al. |
| 5,505,206 A | | 4/1996 | Walloch |

(List continued on next page.)

FOREIGN PATENT DOCUMENTS

| | | |
|---|---|---|
| EP | 0 960 598 A1 | 5/1998 |
| EP | 0 898 935 A1 | 8/1998 |

OTHER PUBLICATIONS

Maynard Ramsey III, MD, PHD; Knowing Your Monitor Equipment; Blood Pressure Monitoring: Automated Oscillometric Devices; 1991 by Little, Brown and Company; pp. 56–67; Tampa, Florida.

Maynard Ramsey III: Medical & Biological Engineering & Computing; Noninvasive automatic determination of mean arterial pressure; Jan. 1979; pp. 11–18; Tampa, Florida.

Primary Examiner—Max F. Hindenburg
Assistant Examiner—Patricia C. Mallari
(74) Attorney, Agent, or Firm—Michael Best & Friedrich LLP

(57) ABSTRACT

A physiological-signal-analysis device for determining a blood pressure value of a patient and a method of operating the device. The device includes a cuff attachable to an extremity of the patient, a pneumatic system connected to the cuff that supplies a fluid to the cuff, a pressure transducer that measures the pressure signal having pressure oscillations, and a control unit connected to the pneumatic system and the pressure transducer. The control unit is operable to acquire a first oscillation having a first fiducial point, acquire a second oscillation having a second fiducial point, calculate a time interval representing a time from the first fiducial point to the second fiducial point, decide against selecting the second oscillation when the time interval is not a substantial integral multiple of a nominal oscillation period, and calculate a blood pressure value based on selected oscillations.

47 Claims, 5 Drawing Sheets

U.S. PATENT DOCUMENTS

| | | |
|---|---|---|
| 5,651,370 A | 7/1997 | Hersh et al. |
| 5,680,867 A * | 10/1997 | Shimazu et al. ............ 600/490 |
| 5,755,669 A * | 5/1998 | Ono et al. ................. 600/494 |
| 5,800,359 A | 9/1998 | Medero et al. |
| 5,853,371 A * | 12/1998 | Inukai et al. ............... 600/483 |
| 5,865,756 A | 2/1999 | Peel, III |
| 5,931,790 A | 8/1999 | Peel, III |
| 6,050,951 A | 4/2000 | Friedman et al. |
| 6,171,263 B1 * | 1/2001 | Sullivan .................... 600/588 |
| 6,500,127 B1 * | 12/2002 | Inukai et al. ............... 600/485 |

* cited by examiner

PHYSIOLOGICAL-SIGNAL-ANALYSIS DEVICE FOR MEASURING A BLOOD PRESSURE AND METHOD This application is a continuation-in-part of U.S. patent application Ser. No. 09/678,650, filed Oct. 4, 2000, issued Jul. 23, 2002, as U.S. Pat. No. 6,423,010, the entire contents of which are incorporated herein by reference.

BACKGROUND OF INVENTION

The invention relates to a physiological-signal-analysis device for measuring a blood pressure, and particularly to a device that applies a pressure to a patient and determines whether a detected pressure oscillation satisfies one or more criteria.

There are many known devices for measuring a patient''s blood pressure. One type of device uses a technique referred to as an oscillometric technique. For this technique, typically, a blood pressure cuff is connected to an arm of the patient and is pneumatically controlled to apply a high pressure to the patient. The pressure is then reduced in steps to a low pressure. For each pressure step (also referred herein as pressure level), a pressure transducer connected with the cuff senses a cuff pressure. The sensed cuff pressure includes the applied pressure and pressure oscillations (also referred to herein as blood pressure oscillations, pressure pulses and blood pressure pulses). The sensed cuff pressure is applied to a control unit that isolates the pressure oscillations and stores two consecutive, matching oscillations at each pressure step. Requiring two consecutive, matching oscillations prevents intermittent artifact from causing the device to seriously err when performing the measurement. Example blood pressure monitors that require two consecutive, matching oscillations are described in RAMSEY M., Blood Pressure Monitoring: Automated Oscillometric Devices, Journal of Clinical Monitoring, 1991, 7 (1), 56–67, which is incorporated herein by reference.

SUMMARY OF INVENTION

The time duration for measuring a blood pressure depends on the magnitude of the high pressure, the difference in pressure between steps, and the amount of time at each step. With the requirement that the device needs to match consecutive oscillations at each level, the blood pressure determination may be unduly prolonged and the patient may be unduly stressed or inconvenienced. The time for each pressure step is established by the time it takes two consecutive cardiac contractions to produce two, roughly equal pressure oscillations in the cuff. For example, if at a particular pressure step first, third, fifth and sixth pulses match while the second and fourth pulses do not, then the step may be unduly long. This is because the prior art system does not proceed to the next pressure step until after the sixth pulse. Accordingly, it would be beneficial to provide a device for measuring a patient''s blood pressure where the device includes criteria that allows two nonconsecutive pulses to be matched at a level.

Additionally, for some embodiments, it is beneficial to provide a device for measuring a patient''s blood pressure where the device relaxes or changes one or more criteria when a known event is occurring. By relaxing one or more criteria, the device allows the measurement to be performed in a timely fashion for some medically unstable patients. Without the relaxed criteria, the measurement may take too long, causing discomfort to the patient and possibly resulting in no blood pressure determination. Relaxing the criteria in a proper fashion will not overly affect the accuracy of the determination.

Accordingly, in one embodiment, the invention provides a method of determining whether an oscillation of a pressure signal acquired from a patient satisfies one or more criteria. The method includes the acts of acquiring a first oscillation having a first fiducial point, acquiring a second oscillation having a second fiducial point, calculating a time interval representing a time from the first fiducial point to the second fiducial point, and determining whether the time interval is a substantial integral multiple of a nominal time interval.

In yet another embodiment, the method provides acquiring a first electrocardiogram (ECG) beat having a first fiducial point, acquiring a first oscillation having a relationship to the first ECG beat, acquiring a second ECG beat having a second fiducial point, acquiring a second oscillation having a relationship to the second ECG beat, calculating a time interval representing a time from the first fiducial point to the second fiducial point, determining whether the time interval is close to an integral multiple of a nominal time interval, and deciding against selecting the second pressure oscillation when the time interval is not close to an integral multiple of a nominal time interval.

In another aspect of the invention, the invention provides a physiological-signal-analysis device for determining blood pressure values of a patient. The device includes a cuff attachable to an extremity of the patient, a pneumatic system connected to the cuff that supplies a fluid to the cuff, a pressure transducer that captures a pressure signal having pressure oscillations, and a control unit connected to the pneumatic system and the pressure transducer. The control unit is operable to acquire a first oscillation having a first fiducial point, acquire a second oscillation having a second fiducial point, calculate a time interval representing a time from the first fiducial point to the second fiducial point, decide against selecting the second oscillation when the time interval is not a substantial integral multiple of an oscillation period, and calculate a blood pressure value based on selected oscillations.

In a further aspect, the invention provides a software program for operating a physiological-signal-analysis device. The software program includes a pneumatic control module for controlling the operation of the pneumatic system, and an analysis module for analyzing input from the pressure transducer and for calculating a blood pressure. The analysis module includes instructions that are implemented for acquiring a first oscillation having a first fiducial point, acquiring a second oscillation having a second fiducial point, calculating a time interval representing a time from the first fiducial point to the second fiducial point, and determining whether the time interval is close to an integral multiple of a nominal time interval.

Other features, advantages and embodiments of the invention will become apparent by consideration of the detailed description and accompanying drawings.

DETAILED DESCRIPTION

Before any embodiments of the invention are explained, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
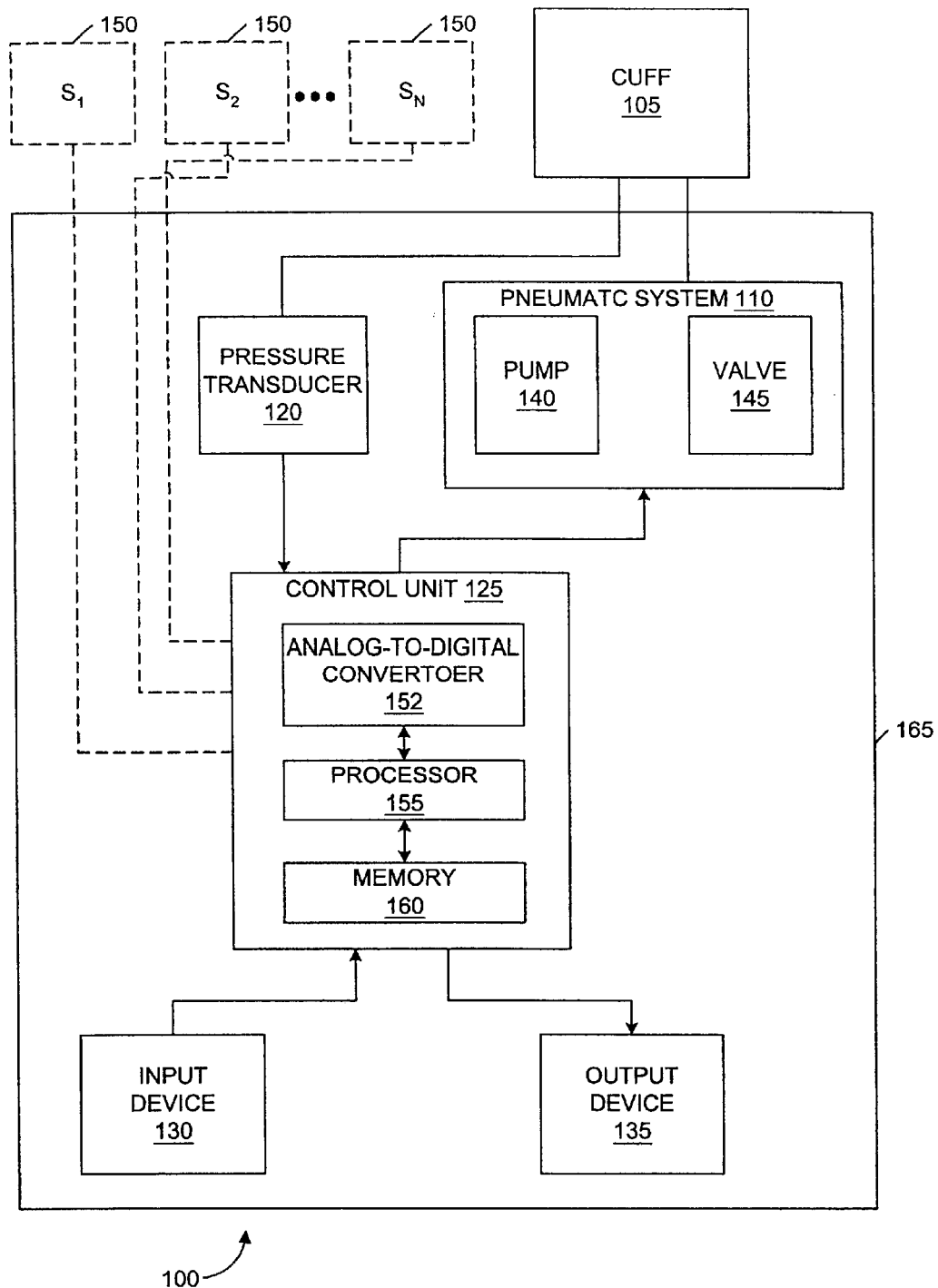
FIG. 1 is a schematic diagram of a physiological-signal-analysis device embodying the invention.

A physiological-signal-analysis device 100 is schematically shown in FIG. 1. As used herein, the term physiological-signal-analysis device includes any device that, among other things, non-invasively monitors blood pressure. An example physiological-signal-analysis device 100 is a blood pressure monitor. It is envisioned that the physiological-signal-analysis device 100 may acquire other physiological signals. For example, if the physiological-signal-analysis device 100 is a patient monitor, then the patient monitor may acquire other physiological signals such as a patient"s ECG, a patient"s respiratory function, etc. Unless specified otherwise, the physiological-signal-analysis device 100 is a blood pressure monitor.

In general terms, the device 100 includes a cuff 105, a pneumatic system 110, a pressure transducer 120, a control unit 125, one or more operator-controlled input devices 130, and one or more output devices 135. The cuff 105 is any conventional inflatable cuff connected to the pneumatic system 110. As used herein, the term "connection," and variations thereof (e.g., connect, connected, connecting, etc.), includes direct and indirect connections. The connection, unless specified, may be by mechanical, electrical, chemical, and/or electro-magnetic means, or any combination of the foregoing (e.g. electro-mechanical). For the embodiment shown, the cuff is mechanically connected to the pneumatic system 110 via one or more tubes.

The pneumatic system 110 includes a pump 140 that pumps a fluid (e.g., air) to the cuff 105. The pressure transducer 120 is connected to the cuff 105 and measures a cuff pressure in the cuff. Typically, the pressure transducer measures the cuff pressure with an additional small varying component (in this case, pressure oscillations) caused by the arterial blood pressure pulsation of a patient"s arm.

In some embodiments, the device 100 may further include other physiological-signal-input devices 150 (shown in phantom) such as other transducers or sensors. For example, the sensors may include ECG electrodes, pulse-oximetry sensors, temperature sensors, etc.

As shown in FIG. 1, the control unit 125 receives input signals from the pressure transducer 120, the other sensors or transducers 150 (if present), and the one or more operator-controlled input devices 130. The input signals include input or data. The control unit analyzes the inputs, and communicates output signals to the pneumatic system 110 and the output devices 135. The output signals include output or data. The control unit 125 includes an analog-to-digital converter 152, processor 155 and a memory 160. The memory 160 includes one or more software modules having instructions, and the processor 155 retrieves, interprets, and executes the instructions of the one or more software modules to control the device 100. Example software modules include a pneumatic system control module for controlling the pneumatic system, and an analysis module for analyzing the input from the pressure transducers and/or the physiological-input devices and for calculating a blood pressure (e.g., systolic pressure, diastolic pressure, mean arterial pressure, etc.). Other software modules will become apparent from the description below.

In general, the software modules stored within the memory 160 instruct the control unit to receive the inputs from the pressure transducer 120, the one or more physiological-signal-input devices 150 (if present), and the one or more operator-controlled input devices 130; to analyze the received inputs; and to provide outputs to the pneumatic system 110 and the one or more output devices 135. The operation and control of the device 100 is discussed in more detail below.

For the embodiment described herein, any processor 155 capable of reading, interpreting and executing software instructions is used with the invention. However, it is envisioned that other processors or controllers may be used with the invention. For example, the processor may be constructed with other analog and/or digital logic circuitry, and may include integrated and/or discrete circuit elements. Also, the control unit 105 may include other elements (e.g., one or more analog-to-digital converters, one or more drivers, one or more power supplies, one or more amplifiers, one or more filters, etc.) that would be apparent to one skilled in the art to support the control unit 125.

The one or more operator-input devices 130 allow an operator (e.g., a technician, nurse, doctor, etc.) to control the device 100 and/or to provide data to the control unit 125. Example operator-input devices 130 include one or more push buttons, one or more trim knobs, a keyboard, a keypad, a touch screen, a pointing device (e.g., a mouse, a trackball), or similar devices. Further and for some aspects of the invention, the one or more operator-controlled input devices 130 may include data storage devices, and other devices or processing units connected via a network. Of course, not all of the operator-controlled input devices 130 are required for operation of the device 100.

The one or more output devices 135 allow the control unit to communicate outputs or data to the operator. Example output devices 135 include a printer, a display (e.g., an LED display, an LCD display, a CRT display, etc.), a storage device (e.g., a magnetic-disc drive, a read/write CD-ROM, etc.), a server or other processing unit connected via a network, audio-output devices, and similar devices. Of course, not all of the output devices 135 are required for operation of the physiological-signal-analysis device 100. Also, the one or more output devices 135 and the one or more operator-controlled input devices 130 may be combined as a single device (i.e., a touch screen).

As shown in FIG. 1, the pneumatic system 110, the pressure transducer 120, the control unit 125, the operator-controlled input devices 130 and the output devices 135 are secured within a central unit 165. However, one skilled in the art will realize that the one or more elements of the monitor 100 may not be secured within the central unit 165. For example, the operator-controlled input device 130 may be a keyboard or keypad that is connected externally to the central unit 165. Thus, the device 100 may be a system incorporating one or more sub-units. As used herein the terms physiological-signal-analysis device and blood pressure monitor encompass units having a number of components, or systems incorporating more than one distinct device.

In operation, the cuff 105 is wrapped around a patient"s arm and an operator initiates a test by depressing an input sequence into the one or more input devices 130. Assuming the operator correctly starts the test, the control unit 125 controls the pneumatic system 110 to inflate (FIG. 2; act 200) the cuff 105 to a pre-determined pressure, typically greater than the systolic pressure of the patient.

For the embodiment shown, when the control unit 125 performs a function, the processor 155 retrieves one or more instructions from memory 160, interprets the received instructions, and executes the interpreted instructions to perform the particular function. For example, if the control unit 125 is inflating the cuff 105, then the processor 155 retrieves, interprets and executes, one or more software instructions to generate one or more signals for controlling the pneumatic system 110. While inflating the cuff 105, the software instructs the processor 155 to acquire a signal from the pressure transducer 120, and analyze the signal to determine whether the cuff pressure is at the desired pressure. Thus, the processor 155 retrieves, interprets and executes the one or more software instructions to control the device 100. For the remainder of the description below and unless specified otherwise, when the control unit 125 performs a function or action, one skilled in the art will realize that, the processor 155 retrieves, interprets and executes one or more software instructions to perform the described function. However, for other embodiments, the control unit 125 performs differently.

At act 205, the control unit 125 controls the pneumatic system 110 to deflate the cuff 105 to a next pressure step (e.g., deflates the cuff by 8 mm Hg.). At act 210, the control unit 125 determines whether an oscillation has been detected. The cuff pressure sensed by the pressure transducer 120 includes the pressure applied to the patient by the cuff 105 and pressure oscillations produced by the patient. The cuff pressure is supplied to the control unit 125, which isolates the pressure oscillations (if present).

The determination of whether an oscillation has been detected may be performed by a variety of different methods. For example, the control unit 125 may analyze the slope of the pressure waveform at various locations past a baseline pressure to determine whether the slope is within the physiological characteristics of an oscillation. For a specific example, the control unit 125 analyzes the pressure waveform after a baseline pressure to determine whether the rising characteristics (e.g., the slope at an initial rise time, the slope at a middle rise time, etc.) of the pressure oscillation is within limits of an expected oscillation. In other embodiments, the control unit 125 analyzes other factors to determine whether an oscillation is present, including the baseline-to-peak pressure, the time from the baseline pressure to the peak pressure, and the slope during a time period after the peak pressure. The qualifiers for determining whether a pulse is detected may be based on set characteristics or measured characteristics of previously matched pulses (discussed below). If an oscillation is detected, then the control unit 125 proceeds to act 215. If no oscillation is detected within a time period, then the control module proceeds to act 235. The control module repeats searching for an oscillation until an oscillation is detected or a total time out or a step time out has occurred.

At act 215, the control unit 125 measures the amplitude of the oscillation, the slope of the oscillation at one or more points, and the time from the baseline to the peak of the oscillation. These measurements are used for determining whether the detected oscillation matches one or more criteria (discussed further below) and, if the measurements match, for performing blood pressure calculations.

At act 220, the control unit 125 checks to see if two pulses have been found at a step. Once a second oscillation is detected, the control unit 125 proceeds to act 225. If a second oscillation is not detected, then the control unit 125 returns to act 207.

At act 225, the control unit 125 performs envelope, period, time to peak, slope and peak matching on the two pulses as is known in the art. At act 230, the control unit 125 determines whether the oscillations satisfy a matching criteria (discussed below with reference to FIG. 3). If the oscillations do not satisfy the matching criteria, then the control unit 125 proceeds to act 207. If the oscillations do satisfy the matching criteria, then the control unit 125 proceeds to act 202.

Figure 3:
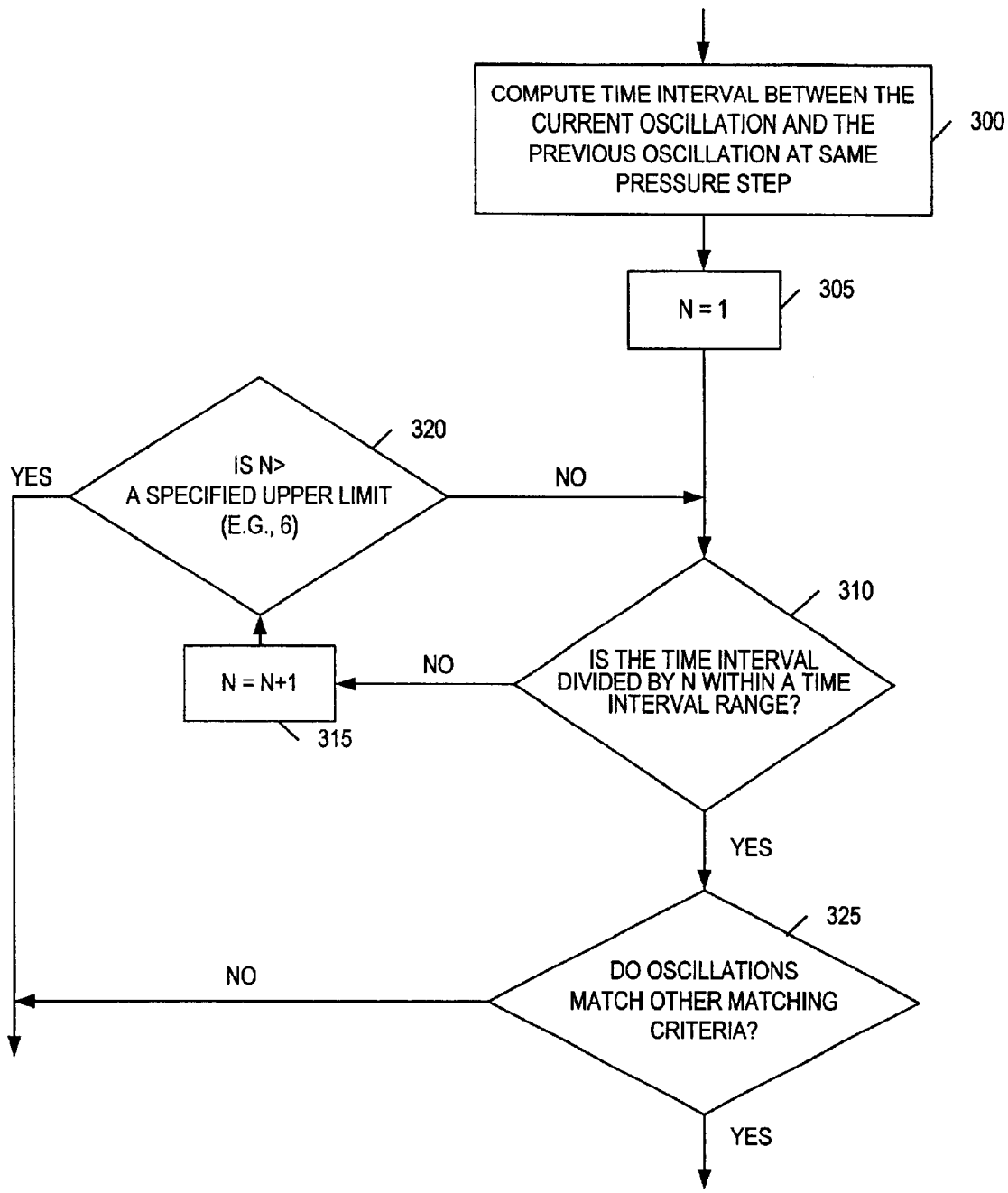
FIG. 3 is a flow chart representing one embodiment for determining whether pressure oscillations satisfy the defined matching criteria.
Figure 4:
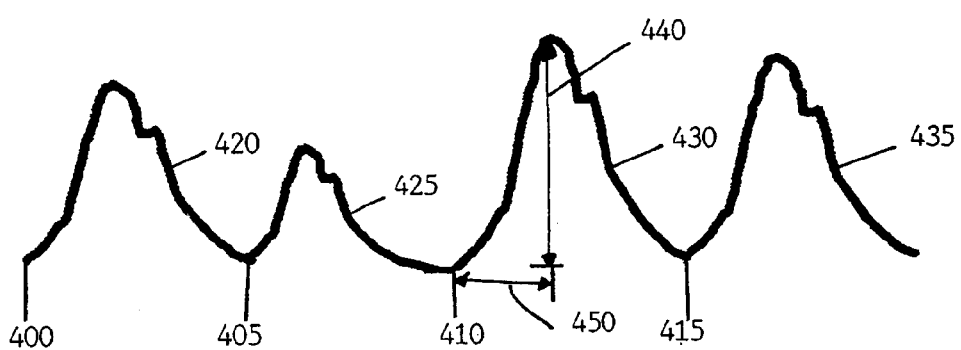
FIG. 4 is a diagram representing a plurality of pressure oscillations.

One embodiment for determining whether the oscillations satisfy a matching criteria is schematically shown in FIG. 3. At act 300, the control unit 125 computes a time interval (also referred to as a pulse period) between like fiducial points of the current and previous oscillations. For example, four pressure oscillations 420, 425, 430 and 435 having four fiducial points 400, 405, 410 and 415, respectively, are shown in FIG. 4. The points 400, 405, 410 and 415 are the beginning of each oscillation 420, 425, 430 and 435, respectively (i.e., when the oscillation is at a baseline). If the control unit 125 is proceeding to act 300 after detecting oscillation 425, then the time interval is the time difference between points 405 and 400. If the control unit 125 is proceeding to act 300 after detecting oscillation 430, then the time interval is the time difference between points 410 and 400 (assuming oscillation 425 was not detected). Unless specified otherwise, the description below assumes that the control unit 125 has just detected oscillation 430, and that oscillation 425 did not satisfy the matching criteria.

As shown in FIG. 3, for acts 305–320, the control unit 125 determines whether the current time interval (e.g., from fiducial point 410 to fiducial point 400) is a multiple number of a nominal time interval. At act 305, the control unit 125 sets a variable N equal to 1. At act 310, the control unit 125 determines whether the current time interval divided by N is within a specified range. For example, the high value for the range may be calculated by multiplying a nominal time interval by a first factor (e.g., 1.3), and the low value for the range may be calculated by multiplying the nominal time interval by a second factor (e.g., 0.7). Of course, the first and second factors may vary. As used herein, the term nominal time interval means a set or calculated time interval used as matching criteria. In one embodiment, the nominal time interval is an average time interval from a recent test performed on the patient. In other embodiments, the nominal time interval is derived from measurements at previous pressure steps. Of course, other methods may be used to calculate the nominal time interval. If the time interval divided by N is within the time interval range, then the control unit 125 proceeds to act 325 (i.e., the time interval is a substantial integral multiple of the nominal time interval.) Otherwise, the control unit 125 proceeds to act 315.

At act 315, the control unit 125 increases the value of N, and at act 320, determines whether the value of N is greater than a specified upper limit (e.g., six). If the value N is greater than the specified upper limit, then the control unit 125 determines that the time interval is not a multiple number of a nominal time interval and returns to act 207. If N is less than or equal to the specified upper limit, then the control unit 125 again determines whether the time interval is a multiple number of the nominal time interval. The control unit 125 cycles through acts 310, 315 and 320 until either a match occurs or the value N is greater than the specified upper limit. For example, the control unit would proceed to act 325 at N=2 for oscillation 430.

Figure 2:
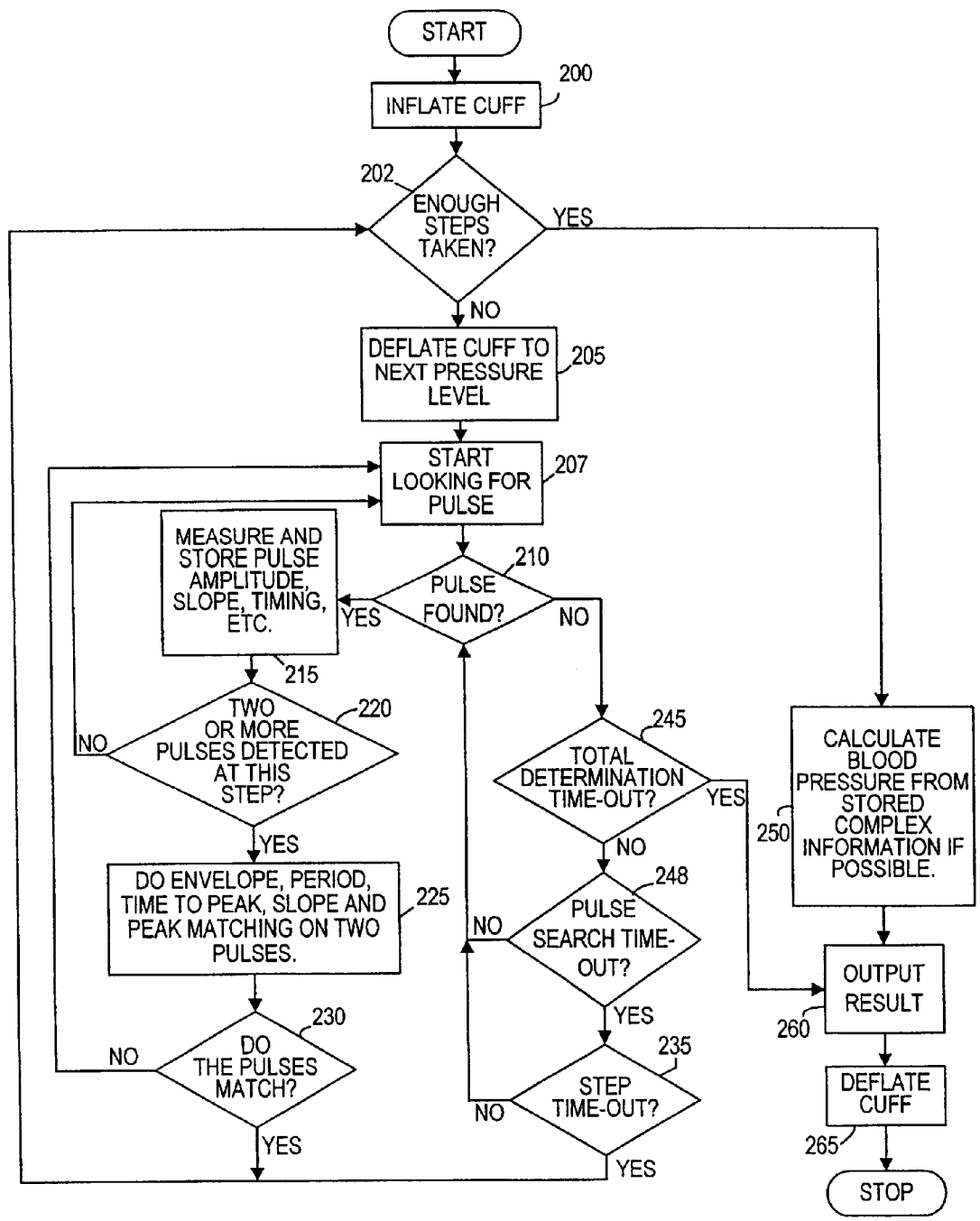
FIG. 2 is a flow chart representing one method of operation of the physiological-signal-analysis device.

At act 325, the control unit 125 analyzes other criteria or characteristics of the oscillations. For example and as shown in FIG. 4, the control unit 125 may determine whether the amplitude 440 is within a nominal amplitude value range, whether one or more recorded slopes are within nominal slope value ranges, and whether the time-to-peak interval 450 is within a nominal time interval range. The time-to-peak interval 450 is the time from the start of the oscillation 430 to the maximum of the oscillation 430. The determination of whether the amplitudes, the one or more slopes and the time-to-peak interval 450 are within nominal ranges may be performed similar to act 310. It is envisioned that not all of the criteria are required and that other criteria may be added. It is also envisioned that the determination of whether the first oscillation 420 (FIG. 4) matches the nominal criteria may be performed earlier after obtaining the first pulse. When two oscillations satisfy the matching criteria (FIG. 3; act 325), the control unit 125 proceeds to act 202 (FIG. 2). Otherwise, the control unit 125 proceeds to act 207 (FIG. 2).

At act 235, the control unit 125 determines whether a time out is exceeded for the pressure step. For example, if the length of time for the pressure step is too long, then the control unit 125 proceeds to act 202. If the time out is not exceeded, then the control unit 125 returns to act 210 to search for the next oscillation. The control unit 125 proceeds until either two oscillations match nominal criteria or the time out is exceeded.

At act 245, the control unit 125 determines whether a timeout for the test is exceeded. If the timeout is exceeded, then the control unit 125 proceeds to act 260, where the control unit 125 deflates the cuff 105 (act 265) and prevents the determination from proceeding further. If the time out is not exceeded, then the control unit 125 returns to act 248. The control unit 125 proceeds through acts 202–265 until the determination is completed or a time out has occurred. Upon completion of the determination, the control unit 125 analyzes the stored data derived from the oscillations (act 250), calculates the pulse rate, systolic, diastolic and mean arterial pressures, and displays the values (act 260).

Embodiments of the invention have been described above with reference to FIGS. 2–4. However, additional embodiments are envisioned. For example, it is envisioned that, when the control unit 125 performs acts 300–320, a time interval between a current oscillation and a previous oscillation may be calculated, where the previous oscillation is at a previous cuff pressure step. For example and with reference to FIGS. 3 and 4, at act 300, the control unit 125 calculates a time interval between a first fiducial point 400 of a previous pulse 420 at a first pressure step and a second fiducial point 410 of a current pulse 430 at a second pressure step. The control unit 125 then proceeds through acts 305 and 315 as shown. For act 320, the software advances to act 310 unless N is greater than a set number (e.g., six) or until a timeout is exceeded.

For another embodiment, other physiological signals acquired from the patient are used to gather additional information. For example, an acquired ECG is used to further analyze whether an acquired oscillation satisfies one or more matching criteria. In one specific embodiment, the control unit analyzes ECG beats, where each pressure oscillation is functionally related to a corresponding ECG beat. The control unit uses this relationship to further determine whether an acquired oscillation is satisfactory for blood pressure calculations. When the control unit detects an oscillation, the control unit measures characteristics of that oscillation and measures characteristics of the related ECG beat (e.g., the timing relationship of the R-wave to the beginning of the pressure oscillation, and the timing relationship of the R-wave to a previous R-wave, etc.).

Figure 5:
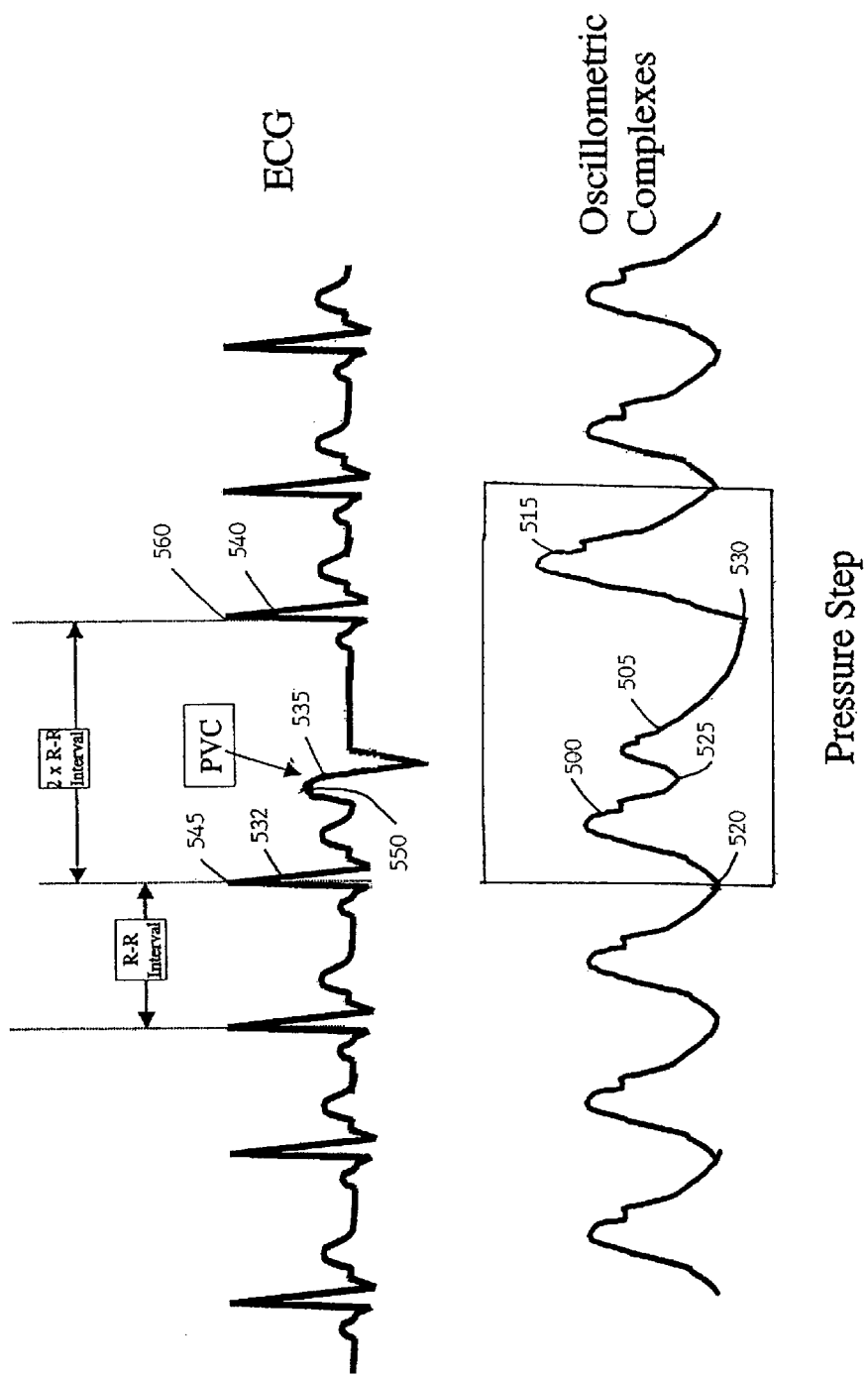
FIG. 5 is a diagram representing a plurality of ECG beats and a plurality of pressure oscillations.

For a specific example and as shown in FIG. 5, the control unit detects pressure oscillations 500, 505 and 515 having beginning points 520, 525 and 530. Functionally related to oscillations 500, 505 and 515 are beats 532, 535 and 540 having R-waves 545, 550 and 560. At act 225, the control unit 125 uses the acquired oscillations 500, 505 and 515 and ECG beats 532, 535 and 540 to determine whether the pressure oscillation satisfies the matching criteria. Specifically, the control unit 125 determines whether a time interval between a first fiducial point of an ECG beat (e.g., the maximum amplitude of the QRS complex) associated with a previous oscillation and a second fiducial point of an ECG beat associated with a current oscillation is a multiple number of a nominal time interval. For example and as shown in FIG. 5, rather than using points 520 and 530 of oscillations 500 and 515, respectively, the control unit 125 uses points 545 and 560 of beats 532 and 540, respectively, when performing acts 300–320. For this embodiment, at act 300, the control unit 125 computes the interval time between the current beat 540 and a previous beat 532. At act 310, the control unit 125 determines whether the time interval divided by N is within a range of the nominal beat. At act 320, the control unit 125 determines whether N is greater than a specified upper limit.

Thus, the invention provides, among other things, a new and useful physiological-signal-analysis device for measuring a blood pressure and method of operating the same. Various features and advantages of the invention are set forth in the following claims.

What is claimed is:

1. A method of determining whether an oscillation of a pressure signal acquired from a patient satisfies one or more criteria, the method comprising the acts of:

acquiring a first oscillation having a first fiducial point;

acquiring a second oscillation having a second fiducial point;

calculating a time interval representing a time from the first fiducial point to the second fiducial point; and determining whether the time interval is an integral multiple of a nominal.

2. A method as set forth in claim 1 wherein the nominal time interval is an average oscillation period.

3. A method as set forth in claim 1 wherein the first fiducial point is the starting point of the first oscillation, and wherein the second fiducial point is the starting point of the second oscillation.

4. A method as set forth in claim 1 wherein the first fiducial point is the maximum slope point of the first oscillation, and wherein the second fiducial point is the maximum slope point of the second oscillation.

5. A method as set forth in claim 1 wherein the first fiducial point is the maximum amplitude point of the first oscillation, and wherein the second fiducial point is the maximum amplitude point of the second oscillation.

6. A method as set forth in claim 1 wherein the act of determining whether the time interval is an integral multiple of a nominal time interval includes determining whether the time interval is within a time interval range.

7. A method as set forth in claim 1 wherein the act of determining whether the time interval is an integral multiple of a nominal time interval includes the acts of setting a variable (N), and determining whether the interval divided by (N) is within a time interval range.

8. A method as set forth in claim 7 wherein the act of determining whether the interval divided by (N) is within a time interval range includes the acts of multiplying the nominal time interval by a first factor to calculate a high value, multiplying the nominal time interval by a second factor to calculate a low value, and determining whether the interval divided by (N) is between the high and low values.

9. A method as set forth in claim 1 wherein the second oscillation has an amplitude, and wherein the method further comprises the act of determining whether the amplitude is within an amplitude range.

10. A method as set forth in claim 9 wherein the amplitude range is a range around an amplitude of the first oscillation.

11. A method as set forth in claim 1 wherein the second oscillation has a slope during a specified interval, and wherein the method further comprises the act of determining whether the slope is within a slope range.

12. A method as set forth in claim 11 wherein the slope range is a range around a slope of the first oscillation.

13. A method as set forth in claim 1 wherein the second oscillation has a time-to-peak interval, the time-to-peak interval representing a time from a starting point of the second oscillation and a point when a maximum amplitude of the second oscillation occurs, and wherein the method further comprises the act of determining whether the time-to-peak interval is within a time-to-peak interval range.

14. A method as set forth in claim 13 wherein the time-to-peak interval range is a range around a time-to-peak interval of the first oscillation.

15. A method as set forth in claim 1 and further comprising the acts of:
 applying a pressure to a patient's extremity; and
 acquiring the first and second oscillations at a same pressure.

16. A method as set forth in claim 1 and further comprising the acts of:
 applying a first pressure to a patient's extremity;
 wherein the act of acquiring the first oscillation occurs when the first pressure is applied to a patient's extremity;
 applying a second pressure to a patient's extremity, the second pressure being less than the first pressure; and
 wherein the act of acquiring the second oscillation occurs when the second pressure is applied to the patient's extremity.

17. A method of determining whether an oscillation of a blood pressure signal satisfies a criteria, the method comprising the acts of:
 acquiring an electrocardiogram (ECG) signal having a first beat and a second beat;
 identifying a first fiducial point on the first ECG beat and a second fiducial point on the second ECG beat;
 acquiring a blood pressure signal having a first oscillation related to the first ECG beat and a second oscillation related to the second ECG beat;
 calculating a time interval between the first fiducial point and the second fiducial point;
 determining whether the time interval is an integral multiple of a nominal time interval; and
 rejecting the second oscillation for use in blood pressure calculations if the time interval is not an integral multiple of a nominal time interval.

18. A method as set forth in claim 17 and further comprising the acts of:
 classifying at least one of the first ECG beat and the second ECG beat; and
 adjusting the nominal time interval when at least one of the first ECG beat and the second ECG beat is an abnormal beat.

19. A method as set forth in claim 17 wherein the act of determining whether the time interval is an integral multiple of a nominal time interval includes determining whether the time interval is within a time interval range.

20. A method as set forth in claim 17 wherein the act of determining whether the time interval is an integral multiple of a nominal time interval includes the acts of setting a variable (N) and determining whether the interval divided by (N) is within a time interval range.

21. A method as set forth in claim 20 wherein the act of determining whether the interval divided by (N) is within a time interval range includes the acts of multiplying the nominal time interval by a first factor to calculate a high value, multiplying the nominal oscillation period by a second factor to calculate a low value, and determining whether the interval divided by (N) is between the high and low values.

22. A method of rejecting an artifact in a blood pressure signal, the method comprising the acts of:
 acquiring an electrocardiogram (ECG) signal having an ECG beat;
 identifying a QRS fiducial point on the ECG beat;
 acquiring a blood pressure signal having an oscillation related to the ECG beat;
 identifying a beginning-of-oscillation fiducial point on the oscillation;
 calculating a QRS-to-oscillation interval between the QRS fiducial point and the beginning-of-oscillation fiducial point;
 determining whether the oscillation is an artifact based on the QRS-to-oscillation interval; and
 rejecting the oscillation for use in blood pressure calculations if the oscillation is an artifact.

23. A physiological-signal-analysis device for determining a blood pressure value of a patient, the device comprising:
 a cuff attachable to an extremity of a patient;
 a pneumatic system connected to the cuff that supplies a fluid to the cuff;
 a pressure transducer that captures a pressure signal having a pressure oscillation; and
 a control unit connected to the pneumatic system and the pressure transducer, the control unit being operable to acquire a first oscillation having a first fiducial point, acquire a second oscillation having a second fiducial point,
 calculate a time interval representing a time from the first fiducial point to the second fiducial point,
 decide against selecting the second oscillation when the time interval is not a an integral multiple of a nominal oscillation period, and
 calculate the blood pressure value based upon selected oscillations.

24. A device as set forth in claim 23 wherein the first fiducial point is the baseline of the first oscillation, and the second fiducial point is the baseline of the second oscillation.

25. A device as set forth in claim 23 wherein the first fiducial point is the maximum slope point of the first oscillation, and the second fiducial point is the maximum slope point of the second oscillation.

26. A method as set forth in claim 23 wherein the first fiducial point is the maximum amplitude point of the first oscillation, and the second fiducial point is the maximum amplitude point of the second oscillation.

27. A device as set forth in claim 23 wherein the second oscillation has a maximum amplitude, and wherein the control unit is further operable to decide against selecting the second oscillation when the maximum amplitude is not within a maximum amplitude range.

28. A device as set forth in claim 23 wherein the second oscillation has a slope, and wherein the control unit is further operable to decide against selecting the second oscillation when the slope is not within a slope range.

29. A device as set forth in claim 23 wherein the second oscillation has a time-to-peak interval, the time-to-peak interval representing a time from a starting point of the second oscillation and a point when a maximum amplitude of the second oscillation occurs, and wherein the control unit is further operable to decide against selecting the second oscillation when the time-to-peak interval is not within a time-to-peak interval range.

30. A device as set forth in claim 23 wherein the control system is further operable to control the pneumatic system such that the cuff applies varying pressure steps to the patient, wherein the first and second oscillations occur at the same pressure step.

31. A device as set forth in claim 23 wherein the control system is further operable to control the pneumatic system such that the cuff applies varying pressure steps to the patient, and wherein the first oscillation occurs at a first pressure step and the second oscillation occurs at a pressure different than the first pressure step.

32. A device as set forth in claim 23 wherein the control unit includes a processor, and a memory having one or more software modules.

33. A device as set forth in claim 23 wherein the device further comprises a plurality of electrodes, and wherein the controller is further operable to acquire an electrocardiogram (ECG) having beats, and to classify the beats.

34. A device as set forth in claim 23 wherein the control unit deciding against selecting the second oscillation when the time interval is not an integral multiple of a nominal oscillation period includes the control unit determining whether the time interval is within a time interval range.

35. A device as set forth in claim 23 wherein the control unit deciding against selecting the second oscillation when the time interval is not an integral multiple of a nominal oscillation period includes the control unit setting a variable (N) and the control unit determining whether the interval divided by (N) is within a time interval range.

36. A device as set forth in claim wherein the control unit determining whether the interval divided by (N) is within a time interval range includes the control unit multiplying the nominal oscillation period by a first factor to calculate a high value, the control unit multiplying the nominal oscillation period by a second factor to calculate a low value, and the control unit determining whether the interval divided by (N) is between the high and low values.

37. A computer program embodied by a computer readable medium capable of being executed by a computer, the computer program capable of causing the computer to operate a physiological-signal-analysis device, the device including a cuff, a pneumatic system, a pressure transducer, and a control unit, the computer program comprising:
a pneumatic control module for controlling the operation of the pneumatic system; and
an analysis module for analyzing input from the pressure transducer and for calculating a blood pressure, the analysis module including instructions that are implemented for
acquiring a first oscillation having a first fiducial point;
acquiring a second oscillation having a second fiducial point;
calculating a time interval representing a time from the first fiducial point to the second fiducial point; and
determining whether the time interval is close to an integral multiple of a nominal time interval.

38. A computer program as set forth in claim 37 wherein the second oscillation has an amplitude, and wherein the analysis module further includes instructions for determining whether the amplitude is within an amplitude range.

39. A computer program as set forth in claim 37 wherein the second oscillation has a slope during a specified interval, and wherein the analysis module further includes instructions for determining whether the slope is within a slope ranges.

40. A computer program as set forth in claim 37 wherein the second oscillation has a time-to-peak interval, the time-to-peak interval representing a time from a starting point of the second oscillation and a point when a maximum amplitude of the second oscillation occurs, and wherein the analysis module further includes instructions for determining whether the time-to-peak interval is within a time-to-peak interval range.

41. A computer program as set forth in claim 37 wherein the instructions for determining whether the time interval is close to an integral multiple of a nominal time interval includes instructions for determining whether the time interval is within a time interval range.

42. A computer program as set forth in claim 37 wherein the instructions for determining whether the time interval is close to an integral multiple of a nominal oscillation period includes instructions for setting a variable (N), dividing the time interval by (N) to create a sub-interval, and determining whether the sub-interval is within a time interval range.

43. A computer program as set forth in claim 42 wherein the instructions for determining whether the sub-interval is within a time interval range includes instructions for multiplying the nominal oscillation period by a first factor to calculate a high value, multiplying the nominal oscillation period by a second factor to calculate a low value, and determining whether the sub-interval is between the high and low values.

44. A method of determining whether an oscillation of a blood pressure signal satisfies a criteria, the method comprising the acts of:
acquiring a first electrocardiogram (ECG) beat having a first fiducial point;
acquiring a first oscillation having a relationship to the first ECG beat;
acquiring a second ECG beat having a second fiducial point;
acquiring a second oscillation having a relationship to the second ECG beat;
calculating a time interval representing a time from the first fiducial point to the second fiducial point;
determining whether the time interval is close to an integral multiple of a nominal time interval; and
deciding against selecting the second pressure oscillation when the time interval is not a an integral multiple of a nominal time interval.

45. A method as set forth in claim 44 wherein the second oscillation includes a maximum amplitude, and wherein the method further comprises the act of determining whether the maximum amplitude is within a maximum amplitude range when the time interval is close to an integral multiple of a nominal time interval.

46. A method as set forth in claim 44 wherein the second oscillation includes a slope, and wherein the method further comprises the act of determining whether the slope is within a slope range when the time interval is close to an integral multiple of a nominal time interval.

47. A method as set forth in claim 44 wherein the second oscillation includes a time-to-peak interval, the time-to-peak interval representing a time from a starting point of the second oscillation and a point when a maximum amplitude of the second oscillation occurs, and wherein the method further comprises the act of determining whether the time-to-peak interval is within a time-to-peak interval range when the first time interval is close to an integral multiple of a nominal time interval.

* * * * *